United States Patent
Souzy et al.

(10) Patent No.: US 9,700,505 B2
(45) Date of Patent: Jul. 11, 2017

(54) COMPOSITION INCLUDING A (METH)ACRYLIC COPOLYMER AND PIGMENT PARTICLES

(71) Applicant: COATEX, Genay (FR)

(72) Inventors: Renaud Souzy, Caluire et Cuire (FR); Jean-Marc Suau, Lucenay (FR); Olivier Guerret, Pern (FR)

(73) Assignee: COATEX, Genay (FR)

( * ) Notice: Subject to any disclaimer, the term of this patent is extended or adjusted under 35 U.S.C. 154(b) by 0 days.

(21) Appl. No.: 14/689,134

(22) Filed: Apr. 17, 2015

(65) Prior Publication Data
US 2015/0283057 A1    Oct. 8, 2015

Related U.S. Application Data

(63) Continuation of application No. PCT/FR2013/052436, filed on Oct. 11, 2013.

(60) Provisional application No. 61/717,695, filed on Oct. 24, 2012.

(30) Foreign Application Priority Data

Oct. 18, 2012  (FR) ..................... 12 59926
Jun. 10, 2013  (FR) ..................... 13 55318

(51) Int. Cl.
*A61K 8/27*     (2006.01)
*A61K 8/29*     (2006.01)
*A61K 8/81*     (2006.01)
*A61Q 17/04*    (2006.01)
*A61K 8/86*     (2006.01)
*A61K 8/91*     (2006.01)

(52) U.S. Cl.
CPC .............. *A61K 8/8152* (2013.01); *A61K 8/27* (2013.01); *A61K 8/29* (2013.01); *A61K 8/8147* (2013.01); *A61K 8/86* (2013.01); *A61K 8/91* (2013.01); *A61Q 17/04* (2013.01)

(58) Field of Classification Search
None
See application file for complete search history.

(56) References Cited

U.S. PATENT DOCUMENTS

| | | | | |
|---|---|---|---|---|
| 4,597,963 | A * | 7/1986 | Deckner | A61K 8/8135 424/59 |
| 5,221,533 | A * | 6/1993 | Perlman | A61K 8/19 424/195.18 |
| 5,607,664 | A * | 3/1997 | Ascione | A61K 8/29 424/401 |
| 5,608,025 | A * | 3/1997 | Kawanishi | C08F 220/34 526/312 |
| 6,090,369 | A * | 7/2000 | Stewart | A61K 8/27 424/401 |
| 6,946,510 | B2 * | 9/2005 | Suau | B01F 17/0028 106/465 |
| 2006/0106129 | A1 * | 5/2006 | Gernon | C09D 5/024 523/122 |
| 2006/0210505 | A1 * | 9/2006 | Clapp | A61K 8/02 424/70.1 |
| 2012/0251474 | A1 * | 10/2012 | Suau | A61K 8/91 424/70.16 |

FOREIGN PATENT DOCUMENTS

EP    0 685 227 A1    12/1995

OTHER PUBLICATIONS

Making Cosmetics, Making Emulsions for Cosmetics, http://www.makingcosmetics.com/articles/02-making-emulsions-for-cosmetics.pdf, retrieved online on Sep. 25, 2015.*
International Search Report dated Dec. 20, 2013 issued in PCT/FR2013/052436 (with English translation).

* cited by examiner

*Primary Examiner* — Jennifer A Berrios
(74) *Attorney, Agent, or Firm* — Oblon, McClelland, Maier & Neustadt, L.L.P.

(57) ABSTRACT

The present invention relates to the use in a sunscreen formulation containing pigment particles as UV-filtering mineral agents, new additives as agents improving the UV-absorbing capacities of said formulations, as well as sunscreen formulations including such agents.

16 Claims, 5 Drawing Sheets

COMPOSITION INCLUDING A (METH)ACRYLIC COPOLYMER AND PIGMENT PARTICLES

CROSS-REFERENCE TO RELATED APPLICATIONS

This application is a continuation of PCT/FR2013/052436, filed Oct. 11, 2013, which claims the benefit of U.S. Provisional Application No. 61/717,695, filed Oct. 24, 2012.

BACKGROUND OF THE INVENTION

Field of the Invention

The present invention relates to the technical field of cosmetics, especially that of sunscreen cosmetic compositions. More particularly, the present invention relates to the use, in cosmetic compositions containing pigment particles as UV-filtering agents, of new additives as agents improving the UV-absorbing capacities of said compositions. The present invention also relates to sunscreen compositions containing such agents.

Description of the Related Art

It is known that UV-B rays with wavelengths comprised between 280 nm and 320 nm cause erythema and skin burns. It is also known that UV-A rays with wavelengths comprised between 320 nm and 400 nm, which are responsible for skin tanning, are also likely to induce an alteration thereof, particularly in the case of sensitive skin or skin that is constantly exposed to solar radiation. It is therefore desirable that sunscreen cosmetic compositions be able to filter UV-A and UV-B radiations.

Many cosmetic compositions intended for solar protection of the skin against UV-A and/or UV-B radiations have been proposed to date. Such compositions traditionally contain a UV radiations filtering agent. There are primarily two categories of UV radiations filtering agents: organic filters and pigment type filters such as the metallic oxides, for example, titanium dioxide and zinc oxide.

In this technical context, a certain number of documents of the prior art describe the use of additives in order to promote the cosmetic properties of the sunscreen compositions that contain them. For example, the use of cross-linked emulsifying copolymers of the C10-C30 alkyl acrylic/acrylate acid type, such as those known as Pemulen® or Carbopol®, the use of which is now very widespread, may be cited.

It turns out however that with certain copolymers of the prior art, the improvement of the compositions cosmetic properties is done at the expense of the UV-absorbing performances of these compositions. Thus, another part of the prior art describes the use of additives whose purpose is, in addition to obtaining beneficial cosmetic properties, the obtaining of sunscreen compositions having protection indexes that are greater than that which may be obtained with the same filtering system.

In this connection, mention can be made of document EP 0 685 227 (L'Oréal) which describes the use of specific polymers to improve the solar protection properties of these compositions. The polymers mentioned in this document are of the cross-linked terpolymer of the methacrylic acid/ethyl acrylate/steareth-10 allyl ether and acrylic acid/vinyl acetate copolymer types.

Also cited is document EP 1 142 564 (L'Oréal) which describes the association in a cosmetic composition of the oil-in-water emulsion type of a particular mixture of polyethylenes with an organic solar protection system.

Other prior art documents describe the use of composite particles whose purpose is both to provide better protection against radiation and to obtain a composition having particular textural properties. Among these, the patent application EP 1 388 550 (Kao Corp) relating to the use of particles consisting of a metal oxide particle coated with a siliconated or fluorinated compound, may be cited. The application FR 2 970 172 (L'Oréal) may also be cited, in which the composite particles include a matrix and an inorganic UV filter. Such particles are formulated in the presence of a hydrophilic dispersant surfactant agent.

Nevertheless, it must be noted that mineral pigment type for example, titanium dioxide ($TiO_2$), zinc oxide (ZnO), cerium oxide ($CeO_2$) and/or iron oxides ($Fe_3O_4$, $Fe_2O_3$) or composite mineral pigments, for example particles of coated titanium dioxide or particles of titanium dioxide having undergone one or several surface treatments of chemical, electronic, mechanochemical and/or mechanical nature, are products whose availability is becoming increasingly limited because they rely only on a natural resource. This leads to an increase in their price which is a problem for the formulators of sunscreen compositions.

The inventors therefore sought a solution to this problem of pigment particles availability of mineral pigments type and of coated mineral pigments type. Specifically, the inventors sought a solution aimed at implementing reduced quantities of pigment particles in sunscreen cosmetic compositions without reducing the properties expected of said compositions.

A certain number of the prior art documents describe the implementation of dispersing agents that have the ability to improve the state of pigment dispersions in cosmetic products. Nevertheless, despite the use of dispersing agents in sunscreen cosmetic formulations, the phenomenon of particles flocculation, notably during storage of the cosmetic composition and in the formation of the film on the skin reduces the filtering effectiveness of agents such as $TiO_2$ and/or ZnO.

BRIEF SUMMARY OF THE INVENTION

A solution to the technical problem of the availability of pigment particles, such as $TiO_2$ and/or ZnO, coated or not, is surprisingly provided by the use of a special copolymer with a specific molecular weight and structure.

In fact, the inventors demonstrate in an advantageous manner that it is possible to significantly reduce the amount of pigment particles in the sunscreen cosmetic composition without reducing the UV-absorbing performances of said composition. This goes against a technical bias in the sunscreen composition field according to which, logically, a composition in which the amount of UV-filtering agents was reduced would no longer offer acceptable solar radiations protection. This technical bias is especially included in the introduction of the patent application FR 2 970 172. The inventors demonstrate moreover that the copolymers according to the invention have no intrinsic UV-absorbing property. The present invention is thus based on a particular combination of a UV radiations filtering agent, more particularly pigment particles according to the invention and a copolymer. In fact, the inventors demonstrate the increase in UV absorbance of a cosmetic composition which combines the copolymers according to the invention, with a specific structure and molecular weight, and pigment particles as filtering agents, in comparison to a cosmetic composition that does not have the copolymers according to the invention, this including when the pigment particles content of said composition has been reduced (for example, by 20 or 40% by weight in relation to the reference).

One object of the present invention is to improve the state of the pigment particles dispersion in the cosmetic composition, with a particular copolymer in order to increase the UV-absorbing performances of the sunscreen compositions.

Another object of the present invention is to promote the UV filtering properties of pigment particles, such as in particular $TiO_2$ and/or ZnO, coated or not, while minimising the necessary amounts of these pigments in the sunscreen compositions containing them.

Another object of the present invention is to reduce the amount of pigment particles, such as TiO2 and/or ZnO, coated or not, without necessarily having to compensate for this decrease by the addition of another pigment to the composition.

Another object of the present invention is to allow a reduction in the amount of pigment particles, such as TiO2 and/or ZnO, coated or not, in sunscreen cosmetic compositions without a profound change in their cosmetic properties, for example without changing the organoleptic, sensory or textural characteristics.

Another object of the present invention is to propose a copolymer that allows an increase, a compensation or an improvement in the UV-absorbing performances of prepared sun creams by reducing the dose of pigment particles, such as TiO2 and/or ZnO, coated or not, without changing the organoleptic properties, with good stability over time.

The present invention therefore concerns the use, in a sunscreen composition containing pigment particles, such as particles of titanium dioxide or zinc oxide, coated or not, as agents for improving the UV-absorbing capacities of the said composition, of a water-soluble comb type copolymer having a (meth)acrylic acid skeleton and poly(alkylene glycol) side chains. The present invention is based on the combination of a UV-filtering agent, namely pigment particles such as $TiO_2$ and/or ZnO, coated or not, and a particular (meth)acrylic copolymer.

The present invention also concerns a sunscreen composition including in a cosmetically acceptable support from 0.1 to 50% by weight of pigment particles such as $TiO_2$ and/or ZnO related to the total weight of the composition as UV-radiations filtering agents and at least one water-soluble comb type copolymer having a (meth)acrylic acid skeleton and poly(alkylene glycol) side chains.

DETAILED DESCRIPTION OF THE INVENTION

Figure 1:
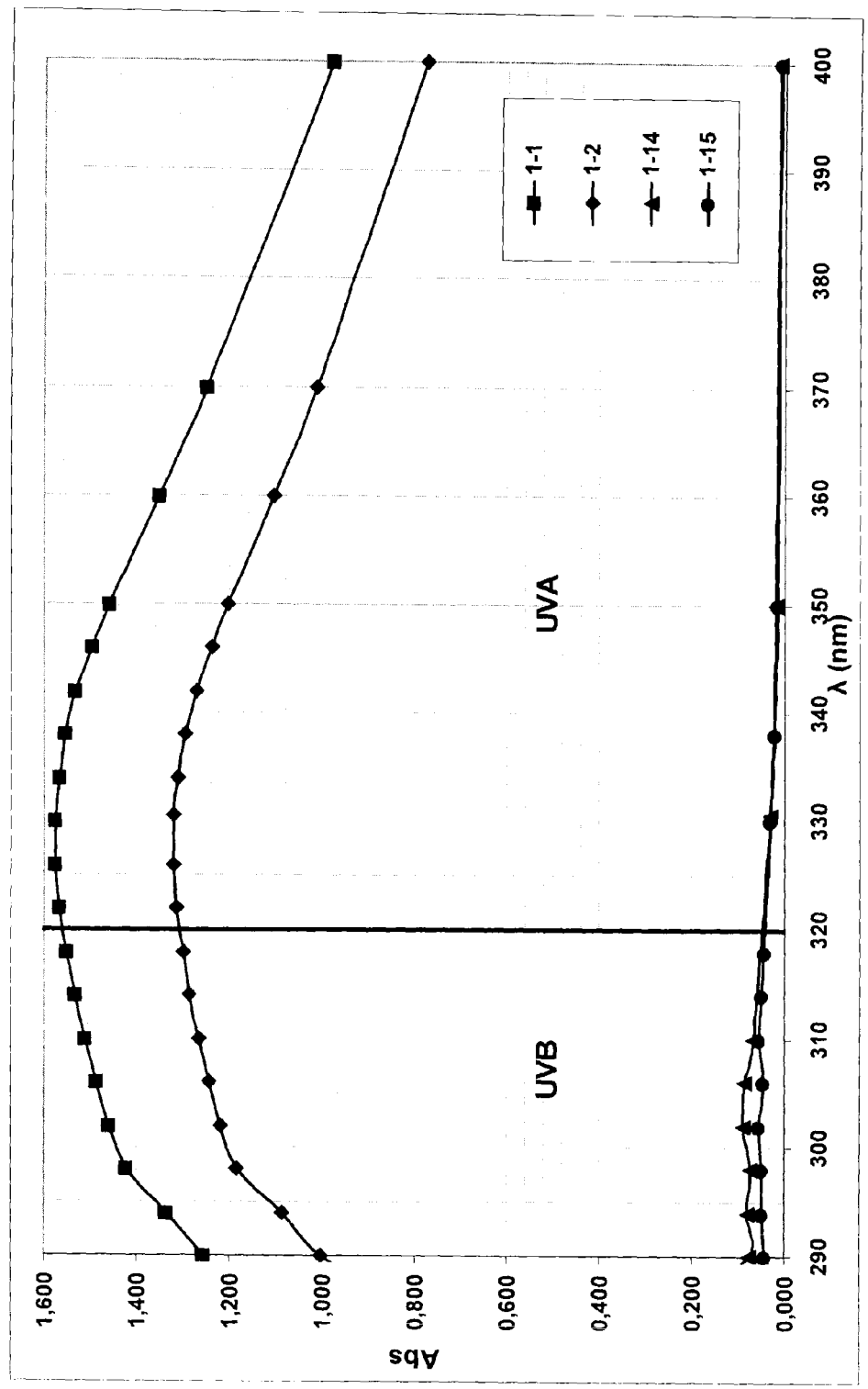
FIG. 1 shows the UV-A and UV-B absorbance spectra described in Example 1.

By "pigment particles" is meant a mineral compound, for example, titanium dioxide ($TiO_2$), zinc oxide (ZnO), cerium oxide ($CeO_2$) and/or iron oxides ($Fe_3O_4$, $Fe_2O_3$), coated or not, or a mixture of these compounds. These pigment particles may, for example, have undergone one or several surface treatments of chemical, electronic, mechanochemical and/or mechanical nature. These particles may have undergone a surface treatment by substances, for example of hydrophobic, hydrophilic or mineral nature. For example, for the surface treatment of the pigment particles, one or several of the following compounds may be used: aminoacids, beeswax, fatty acids, fatty alcohols, anionic surfactants, lecithins, sodium, potassium, zinc, iron or aluminium salts of fatty acids, metal alcoxydes (of titanium or aluminium), polyethylene, silicones, proteins (collagen, elastin), alcanolamines, silicium oxides, iron oxides or sodium hexametaphosphate. The pigment particles according to the invention have UV-radiations filtering properties and thus constitute a UV-A filter and/or a UV-B filter. These particles are thus characterized by their photoprotective activity. They may be in the form of micrometric and/or sub-micronic and/or nanometric particles. The structures of these particles may be amorphous and/or crystalline and in the rutile and/or anatase form for $TiO_2$. The $TiO_2$ particles are conventionally obtained by conventional industrial processes from ore, for example by a sulphate or chloride process. According to the invention, the pigment particles are in the pre-dispersed form (for example, suspensions or dispersions in a liquid) or in the powder form. Such particles are available commercially.

By "poly(alkylene glycol)" is meant an alkylene glycol polymer derived from an olefinic oxide. The poly(alkylene glycol) according to the present invention is, for example, the poly(ethylene glycol), the poly(propylene glycol), the poly(butylene glycol) or a poly(alkylene glycol) containing a proportion of the oxy-ethylene group and/or a proportion of the oxy-propylene group and/or a proportion of the oxy-butylene group. The poly(alkylene glycol) according to the present invention may, for example, include a dominant proportion of the oxy-ethylene group in association with a secondary proportion of the oxy-propylene group. Some specific examples of alkylene glycol polymers include: poly(alkylenes glycols) having an average molecular weight of 1,000, 4,000, 6,000, 10,000 and 20,000 g/mol (in the case of the poly(ethylenes glycols) called PEG-1,000, PEG-4,000, PEG-6,000, PEG 10,000, PEG 20,000), the polyethylene polypropylene glycols having an ethylene oxide percentage comprised between 20 and 80% by weight, and a propylene oxide percentage comprised between 20 and 80% by weight.

Specifically, the copolymer according to the invention consists of:
a) at least one acrylic acid monomer and/or one methacrylic acid monomer and/or any one of their salts,
b) at least one monomer of formula (I):

according to which:
R represents a polymerisable unsaturated function, notably acrylate, methacrylate, methacrylurethane, vinyl or allyl,
R' designates hydrogen or an alkyl group having from 1 to 4 carbon atoms,
X represents a structure having n unit(s) of ethylene oxide EO and m unit(s) of propylene oxide PO, arranged in block, alternatively or randomly, m and n are 2 integers comprised between 0 and 150, at least one of which is non-zero, said copolymer having a molecular mass comprised between 25,000 g/mol and 50,000,000 g/mol as determined by Gel Permeation Chromatography (GPC).

Certain (meth)acrylic comb copolymers are described in the technical sector of cosmetic compositions. In particular, the patent application FR 2 973 241 (Coatex) describes shampoos in which they are incorporated and confer a more pronounced styling and rinse elimination effect. However, this patent application does not describe the effect associated with the use of a particular (meth)acrylic copolymer as an agent for improving the UV-absorbing performances of sunscreen compositions incorporating pigment particles. Nor does this application describe sunscreen compositions having such characteristics.

The patent application FR 2 974 502 describes the use of certain (meth)acrylic comb copolymers as colour developing agents in a cosmetic composition for makeup, such copolymers having a molecular mass comprised between 20,000 and 250,000 g/mol. This patent application nevertheless does not describe the effect associated with the use of a particular (meth)acrylic copolymer as an agent for improving the UV-absorbing performances of sunscreen compositions incorporating titanium dioxide and/or zinc oxide particles.

The patent application Ser. No. 12/02,617 filed on Oct. 2, 2012, not yet published (Coatex), describes the use of certain (meth)acrylic comb copolymers to homogenize cosmetic compositions of the mascara type including a film-forming polymer and a dye mineral pigment of the iron oxide type. Cosmetic compositions of the mascara type do not contain $TiO_2$ and/or ZnO.

According to one embodiment of the present invention, the copolymer does not include hydrophobic monomer, such as for example, those chosen from the group consisting of styrene, para-tertio-butyl-styrene, (meth)acrylic esters having from 1 to 4 carbon atoms on the ester group.

The compositions according to the present invention are sunscreen compositions. These compositions are again called anti-solar compositions or solar-protective compositions intended to filter, block or absorb UV radiations ("UV blocker", "UV filter" or "UV absorber").

By "agent improving the UV-absorbing capabilities of sunscreen compositions" is meant an agent that enables obtaining a cosmetic product whose UV-A and/or UV-B radiations absorption capacities are improved. In an equivalent manner, the terms "UV-absorbing capacity developer agent" are used. In the context of the present invention, the terms "to improve", "improving agent" or "developer agent" mean to increase or respectively imply an increase in the absorbancy values of the UV spectrum at wavelengths at least comprised between 310 and 340 nm, for example comprised between 290 and 400 nm, compared to those obtained for a same sunscreen formulation that contains a same determined amount of pigment particles, but no agent according to the invention.

Without wishing to be bound by any theory with regard to the results obtained, the inventors are of the opinion that the copolymers according to the invention have properties that allow to space the pigment particles in formulations, but also to maintain the separation of these particles during the step of film formation on the surface of the skin, and thus to improve the optical path of the light.

The measurement of the UV absorbancy of the sunscreen composition is performed by means of a spectrometer using a sample of the compositions diluted in isopropanol.

The pigment particles which are consistent with the invention have preferably an average size of elementary particle greater than 5 nm and lower than 100 nm. According to one embodiment particularly preferred of the invention, this size varies preferably from 10 nm to 50 nm.

As indicated above, the pigment particles may be coated or not.

The coated pigment particles are pigments which have undergone one or several surface treatments of chemical, electronic, mechanochemical and/or mechanical nature with compounds such as aminoacids, beeswax, fatty acids, fatty alcohols, anionic surfactants, lecithins, sodium, potassium, zinc, iron or aluminium salts of fatty acids, iron alcoxydes (of titanium or aluminium), polyethylene, silicones, proteins (collagen, elastin), alcanolamines, silicium oxides, iron oxides or sodium hexametaphosphate.

The silicones used for the pigment particles coating according to the invention are, for example, chosen in the group containing alkyl silanes, polydialkylsiloxanes and polyalkylhydrogenosiloxanes. For example, the silicones are chosen in the group containing the octyl trimetyl silane, polydimethylsiloxanes and polymethylhydrogensiloxanes.

The pigment particles according to the invention may have undergone several treatments. For example, before their treatment by silicones, they may have been treated by other surface agents, particularly by cerium oxide, alumina, silica, aluminium compounds, silicium compounds or their mixture.

Some examples of pigment particles according to the invention and commercially available are for example titanium dioxide particles coated with:
  silica and eventually iron oxide,
  silica and/or alumina and eventually aluminium stearate,
  alumina,
  silica, alumina and alginic acid,
  alumina and aluminium laurate,
  iron oxide and iron stearate,
  zinc oxide and zinc stearate,
  silica, alumina and treated by a silicone,
  silica, alumina, aluminium stearate and treated by a silicone,
  silica and treated by a silicone,
  alumina and treated by a silicone,
  triethanolamine,
  polydimethylsiloxane (PDMS),
  stearic acid or
  sodium hexametaphosphate.

Some examples of coated titanium dioxide particles commercially available are:
  products of the range SUNVEIL (Ikeda Corporation),
  products of the range MICROTITANIUM DIOXIDE (Tayca),
  products of the range TIOVEIL™ or SOLAVEIL™ (Croda),
  products of the range EUSOLEX® (Merck),
  products of the range TIPAQUE (Ishihara),
  products of the range TTO (Miyoshi Kasei),
  products of the range UV-TITAN (Sachtleben),
  products of the range TRIshield (Tri-K),
  products of the range DAITOPERSION (Daito Kasei) and
  products STT (Kobo).

Some examples of pigment particles according to the invention and commercially available are, for example, non-coated titanium dioxide particles sold under the commercial names:
  MICROTITANIUM DIOXIDE (Tayca),
  P25 (Degussa),
  UFTR (Miyoshi Kasei),
  MIRASUN (Rhodia) and
  Some of the products of the range TIOVEIL™ (Croda).

Some examples of pigment particles according to the invention and commercially available are, for example, non-coated zinc oxide particles sold under the commercial names:
- Z-COTE (BASF),
- NANOX (Elementis) and
- NANOGUARD® and NANOTEK® (Nanophase Technologies Corporation).

Some examples of pigment particles according to the invention and commercially available are, for example, zinc oxide particles:
- coated by polymethylhydrogenesiloxane,
- coated by perfluoroalkyl phosphate and copolymer based on perfluoroalkylethyl dispersed in cyclopentasiloxane,
- coated by silicone grafted acrylic polymer, dispersed in cyclodimethylsiloxane,
- coated by silica and polymethylsilsesquioxane,
- treated by alumina and dispersed in the mixture ethylhexyl methoxycinnamate/PVP-hexadecene copolymer/methicone,
- dispersed at 55% in C12-C15 benzoate alcohols with hydroxystearic acid polycondensate,
- in dispersion at 40% in Finsolv TN, C12-C15 benzoate alcohols and
- in dispersion in oxyethylened cyclopolymethylsiloxane/polydimethylsiloxane, containing 30% or 50% of zinc nano-oxides coated by silica and polymethylhydrogensiloxane.

Some examples of coated zinc oxides particles commercially available are:
- products of the range OXIDE ZINC CS (Toshibi),
- products of the range NANOGUARD® and NANOTEK® (Nanophase Technologies Corporation),
- products of the range DAITOPERSION (Daito Kasei),
- products of the range NANOX GEL (Elementis),
- products of the range ESCALOL or gamme Z (ISP) and
- products of the range SPD (Shin-Etsu).

Some examples of pigment particles according to the invention and commercially available are, for example, non-coated iron oxide particles sold under the commercial names:
- NANOGUARD® et NANOTEK® (Nanophase Technologies Corporation) and
- TY-220 (Mitsubishi).

Some examples of coated iron oxide particles commercially available are:
- NANOGUARD® et NANOTEK® (Nanophase Technologies Corporation).

Formulations which contains pigment particles mixtures may also be cited, notably those of titanium dioxide and cerium dioxide, such as the mixture of titanium dioxide/cerium dioxide coated by silica as well as the mixture of titanium dioxide/zinc dioxide coated by alumina, silica and silicone or the mixture titanium dioxide/zinc dioxide coated by alumina, silica and glycerol.

The sunscreen composition according to the invention also contains a water-soluble copolymer which, according to one aspect of the present invention, has a molecular mass comprised between 300,000 and 50,000,000 g/mol, for example between 300,000 and 20,000,000 g/mol as determined by Gel Permeation Chromatography (GPC).

According to one aspect of the present invention, the water-soluble copolymer has a molecular mass comprised between 300,000 and 1,000,000 g/mol as determined by Gel Permeation Chromatography (GPC).

According to another aspect of the present invention, the water-soluble copolymer has a molecular mass comprised between 1,000,000 and 15,000,000 g/mol.

The sunscreen composition according to the invention also contains a water-soluble copolymer which, according to another aspect of the present invention, has a molecular mass comprised between 25,000 and 15,000,000 g/mol, for example between 25,000 and 1,000,000 g/mol, as determined by Steric Exclusion Chromatography (SEC) also called Gel Permeation Chromatography (GPC).

According to one aspect of the present invention, the water-soluble copolymer has a molecular mass comprised between 25,000 and 500,000 g/mol, as determined by Steric Exclusion Chromatography (SEC) also called Gel Permeation Chromatography (GPC)

According to another aspect of the present invention, the water-soluble copolymer has a molecular mass comprised between 25,000 and 400,000 g/mol.

According to one aspect of the invention, said water-soluble copolymer is such that n is a non-zero integer less than 150 and m is an integer comprised between 0 and 150. According to this aspect of the invention, m possibly takes the value zero, which means that the poly(alkylene glycol) side chains of the copolymer, according to this aspect of the invention only include ethylene oxide units, in other words, according to this aspect of the invention, they are poly(ethylene glycol) side chains.

According to one aspect of the invention, said water-soluble copolymer is such that n is an integer comprised between 15 and 150 and m is an integer comprised between 0 and 150.

According to one aspect of the invention, said water-soluble copolymer is such that n and m are two integers, at least one of which is non-zero and n+m>17.

According to another aspect of the invention, said water-soluble copolymer is such that n and m are two integers, at least one of which is non-zero and n+m>50.

According to another aspect of the invention, the R group of the monomer of formula (I) represents the methacrylate group.

According to another aspect of the invention, the R' group of the monomer of formula (I) represents H or $CH_3$.

According to still another aspect, the R group of the monomer of formula (I) represents the methacrylate group, and the R' group of the monomer of formula (I) represents H.

According to one aspect of the present invention, said copolymer consists, in relation to the total weight of the copolymer, of:
  a) 5 to 19% by weight of acrylic acid and/or methacrylic acid monomers and/or any one of their salts, and
  b) 81 to 95% by weight of at least one monomer of formula (I).

According to still another aspect, said copolymer consists, in relation to the total weight of the copolymer, of:
  A1) 5 to 10% by weight of acrylic acid monomers and/or any one of its salt,
  A2) 5 to 9% by weight of methacrylic acid monomers and/or any one of its salt and
  B) 85 to 95% by weight of at least one monomer of formula (I).

According to one aspect of the invention, said composition includes from 0.05 to 5% by weight of active material of said copolymer in relation to the total weight of the composition.

According to one aspect of the invention, said composition includes from 0.1 to 3% by weight of active material of said copolymer in relation to the total weight of the composition.

According to one aspect of the invention, said composition includes from 0.2 to 50% by weight of pigment particles such as described above.

According to another aspect of the invention, said composition includes from 0.4 to 40% by weight of particles of these pigment particles, for example from 0.4 to 30% by weight.

According to one aspect of the invention, said formulation includes at least titanium dioxide and/or zinc oxide and/or cerium oxide and/or iron oxides, coated or not.

According to another aspect of the invention, said formulation includes in addition another mineral pigment filler selected from the group consisting of calcium carbonate, zinc oxide, kaolin and a silicate.

According to yet another aspect, the pigment mineral fillers of the sunscreen formulation of the present invention consist of:
- from 30 to 90% by weight of titanium dioxide and/or zinc oxide particles, coated or not, and
- from 10 to 70% by weight of at least one other pigment mineral filler, coated or not, selected from the group consisting of calcium carbonate, zinc oxide, kaolin and a silicate.

The sunscreen formulations of the present invention potentially contain additional organic photoprotective UV-A and/or UV-B agents, hydrophilic, lipophilic or non-water-soluble in commonly used cosmetic solvents.

Said other complementary hydrophilic or lipophilic organic photoprotective agents are for example chosen from among anthranilates: derivatives of dibenzoylmethane, cinnamic derivatives, salicylic derivatives, camphor derivatives, benzophenone derivatives, diphenylacrylate derivatives, triazine derivatives, benzotriazole derivatives, benzalmalonate derivatives, benzimidazole derivatives, imidazolines derivatives, bis-benzo-azolyle derivatives, para aminobenzoic acid derivatives, methylene bis-(hydroxyphenyl benzotriazole) derivatives, benzoxazole derivatives, filtering polymers, filtering silicones, alkylstyrene dimeric derivatives, 4,4-diaryl-butadienes and their mixtures.

The additional solar protective agents may be present in the formulations according to the invention in proportions from 0.01 to 20% by weight in relation to the total weight of the composition, for example from 0.1 to 10% by weight in relation to the total weight of the formulation.

Compositions that are consistent with the present invention may also contain classical cosmetic additives chosen from among softeners, humectants, opacifiers, stabilizers, emollients, silicones, anti-foaming agents, perfumes, preservatives, anionic, cationic, non-ionic, zwitterionic or amphoteric surfactants, fillers, propelling agents, alkalinising or acidifying agents or any other ingredient commonly used in the cosmetic and/or dermatologic field.

The sunscreen composition medium according to the present invention is a physiologically and/or cosmetically acceptable medium. It may, for example, be monophasic of the aqueous or non-aqueous/anhydrous type, i.e. essentially consisting of one or more oils.

The composition according to the present invention may also be multiphasic, i.e. it may include several phases. For example, the composition according to the present invention may be biphasic and include at least one anhydrous phase containing at least one polar oil.

The compositions according to the invention may be in any appropriate forms for topic application, notably in aqueous gels form, in emulsion forms obtained by dispersion of a fatty phase (also called oiled phase) in an aqueous phase (O/W) or inversely (W/O) or of several emulsions (for example W/O/W or O/W/O or O/O/W). They may be more or less fluids and have the aspect of a white or coloured cream, an ointment, a milk, a lotion, a serum, a paste, a powder, a solid stick and eventually be aerosol conditioned and be presented in the form of foam or spray. These compositions are prepared according to usual methods known to the art.

Thus, according to one aspect of the present invention, the sunscreen composition includes, in relation to the total weight of the composition, from:
a) 10% to 99.9% by weight of aqueous phase,
b) 0.1% to 90% by total weight of non-aqueous phase,
the sum of a)+b) being equal to 100%.

According to another aspect of the present invention, the sunscreen composition includes, in relation to the total weight of the composition, from:
a) 15% to 99.5% by weight of aqueous phase,
b) 0.5% to 85% by total weight of non-aqueous phase,
the sum of a)+b) being equal to 100%.

According to still another aspect of the present invention, the sunscreen composition includes, in relation to the total weight of the composition, from:
a) 50% to 70% by weight of aqueous phase,
b) 30% to 50% by total weight of non-aqueous phase,
the sum of a)+b) being equal to 100%.

The aqueous phase of the composition may consist of a mixture of water and organic solvents that are miscible with water (miscibility in water greater than 50% by weight at 25° C.). These solvents are, for example, chosen from among the lower monoalcohols containing from 1 to 5 carbon atoms such as ethanol, isopropanol, the glycols containing from 2 to 8 carbon atoms such as propylene glycol, ethylene glycol, 1,3-butylene glycol, dipropylene glycol, the C3-C4 ketones, the C2-C4 aldehydes and the ethoxylated alcohols.

The non-aqueous phase (or fatty phase) of the cosmetic composition according to the present invention is likely to include natural or synthetic ingredients that are immiscible with water, liquids at room temperature (25° C.) and/or solids at room temperature, which may in particular be chosen from the group consisting of waxes, oils, pasty fatty substances, gums and their mixtures.

One object of the present invention is also a preparation process for a sunscreen composition which consists of implementing the copolymer according to the invention.

The sunscreen composition according to the present invention is generally non-rinsed, but it may be rinsed if it is a cleaning product notably foaming.

The invention has also as object a cosmetic treatment process of a keratinic material such as the skin, lashes, eyebrows, nails or mucous membranes characterized in that a composition as defined above is applied on the keratinic material.

According to another aspect, the invention also relates to a cosmetic whole including:
i) a container having at least one compartment, said container being closed by a closure element and
ii) a composition as described previously and arranged into said compartment. The container may be in all the appropriate forms. It may notably be in the form of a flask, a tube, a pot, a case, a box, a packet or a housing.

Said copolymer according to the invention is obtained by known processes of conventional radical copolymerization in solution, in direct or inverse emulsion in bulk, in suspension or precipitation in suitable solvents, in the presence of known starters and transfer agents, or again, by processes of controlled radical polymerization such as the method known as Reversible Addition Fragmentation Transfer (RAFT), the method known as Atom Transfer Radical Polymerization (ATRP), the method known as Nitroxide Mediated Polymerization (NMP), or again, the method known as Cobaloxime Mediated Free Radical Polymerization.

The following examples will allow a better understanding of the present invention, without however limiting the scope.

EXAMPLES

In each of the following examples, the molecular mass of the copolymers according to the invention is determined by Gel Permeation Chromatography (GPC).

Such a technique makes use of a WATERS™ liquid chromatograph apparatus equipped with two detectors. One of these detectors combines the static dynamic scattering of light at an angle of 90°, with the viscometry measured by a MALVERN™ VISCOTEK™ viscometer detector. The other of these detectors is a refractometric concentration detector of the WATERS™ trademark.

This liquid chromatography apparatus is equipped with steric exclusion columns properly chosen by the person skilled in the art in order to separate the different molecular weights of the polymers studied. The elution liquid phase is an aqueous phase containing 1% $KNO_3$.

In detail, as a first step, the polymerization solution is diluted to 0.9% dry in the GPC eluent which is a 1% $KNO_3$ solution. Then it is filtered to 0.2 µm. 100 µL are then injected into the chromatography apparatus (eluent: a 1% $KNO_3$ solution).

The liquid chromatography apparatus contains an isocratic pump (WATERS™ 515), the flow rate of which is adjusted to 0.8 ml/min. The chromatography apparatus also includes a furnace which itself includes the following system of columns in serie: a 6 cm long, 40 mm ID pre-column of the GARD COLUMN ULTRAHYDROGELWATERS™ type, a 30 cm long, 7.8 mm ID linear column of the ULTRAHYDROGEL WATERS™ type and two 30 cm long, 7.8 mm ID 120 ANGSTROM ULTRAHYDROGEL WATERS™ type columns. The detection system consists on the one hand of a refractometric detector of the RI WATERS™ 410 type, and on the other, of a viscometer and light scattering at an angle of 90° dual detector of the 270 DUAL DETECTOR MALVERN™ type. The furnace is brought to a temperature of 55° C., and the refractometer is brought to a temperature of 45° C.

The chromatography apparatus is calibrated with a single standard of PEO 19 k of the PolyCAL™ MALVERN™ type.

In the examples that follow, the measurement of ultraviolet absorbance (UV-A & UV-B) is done as follows:

The measurements are carried out on a Genesys 10 UV™ Spectrometer (Cole Parmer) equipped with Rotilabo-Einmal Kuvetten PS, 4.5 mL cuvettes. Practically, the apparatus is pre-heated 10 minutes before use. A first measurement is carried out by means of a cuvette filled with 3.8 ml of isopropanol (the "white"). The measurement is then carried out using a cuvette filled with 3.8 mL of the homogeneous solution to be tested, i.e. 0.05 g of the sunscreen formulation to be tested, diluted in 40 g of isopropanol. The absorbance is then measured at each wavelength between 290 nm and 400 nm.

The organoleptic properties of different sunscreen compositions formulated at t=1 month are also evaluated. The evaluation is performed at room temperature.

The following criteria are taken into account:

Slump (coverage), Texture (smooth, presence of lumps, grains, "custard-like" or fluid appearance), Odour (presence or not of an odour), Colour (variation of the homogeneity), Surface (smooth or not smooth).

The viscosity of said formulations is measured using a Brookfield RVT model viscometer. Before the viscosity is measured, each of the formulations is left to rest for 24 hours at 25° C. The spindle must be centred over the opening of the flask. The viscosity is then measured at 20 rpm using the appropriate module. The viscometer is left to turn until the viscosity is stable.

Finally, the visco-elasticity (or consistency) of different formulations is determined using a Haake—RheoStress RS 150 type rheometer. The variation of the module G* (Pa) as a function of the stress i (scan from 0 to 800 Pa) is measured at 25° C. using the cone-plate (1°) module.

In addition, a stability test of different sunscreen formulas is carried out:
  at t=3 months—Sample conditioned at 45° C.,
  at t=1 week—Sample conditioned at 60° C. and
  Sample having undergone a number of freeze/thaw cycles.

The following potential instabilities are observed: dephasing, creaming, bleeding, liquid release, deposit/sedimentation.

Example 1—Sun Cream

This example illustrates the use of an agent according to the invention in an SFP 25 sun cream formulation based on the following ingredients (the figures in the last column indicate the mass percentages in relation to the total weight of the composition):

TABLE 1

| Phase | Ingredient | Amount |
|---|---|---|
| Phase A | A-1 DI Water | QSP 100 |
| | A-2 Protachem ™ Na2-P (Protameen) | 0.05 |
| | A-3 Methocel ® E4M PREM (Dow) | 0.1 |
| | A-4 AMP-Ultra ™ PC 2000 (Dow) | 0.30 (Qsp pH 6.70-7.00) |
| | A-5 Butylene glycol | 1.0 |
| | A-6 Glycerin | 2.0 |
| | A-7 Glucam ™ E-20 Humectant (Lubrizol) | 2.0 |
| Phase B | B-8 Crodamol ™ DA-LQ-(Croda) | 4.0 |
| | B-9 Shercemol ™ CO Ester (Lubrizol) | 2.0 |
| | B-10 Crodamol ™ DIPD-LQ-(MV) (Croda) | 1.0 |
| | B-11 Glucate ™ SS Emulsifier (Lubrizol) | 0.1 |
| | B-12 Pemulen ® TR-1 (Lubrizol) | 0.2 |
| | B-13 Carbopol ® Ultrez 21 (Lubrizol) | 0.2 |
| Phase C | C-14 Parsol ® TX (DSM) | Y |
| | C-15 Polymer | Z |
| Phase D | D-16 Nipaguard ™ PDU (Induchem) | 1.0 |

Formulation Preparation Protocol:
  Phase A: the different ingredients are introduced under agitation and the medium is heated to 65° C.,
  Phase B: in another beaker, all the ingredients are mixed except B-12 and B-13, and they are heated to 65° C. under agitation,
  After obtaining a homogeneous phase B, ingredients B-12 and B-13 are dispersed under agitation, Phases A and B are mixed so as to obtain a viscous emulsion, Phase C: under very gentle agitation, polymer C-15 (if present) and the C-14 titanium dioxide (in the form of a powder) are added, The formulation is completed by adding ingredient D-16 and The pH is measured, and a check is made to ensure that it is between 6.7 and 7.0.

Table 2 summarizes all the polymers that were used as ingredient C-15 as part of the tests in the present example 1.

It is noted that the amount of titanium dioxide indicated in the table is expressed as magnitude Y, i.e. a mass percentage in relation to the total weight of the composition.

For example, if Y is equal to 5%, 5 g of C-15 are added for a formulation of 100 g of finished product.

Also, to the extent that the amount of titanium dioxide is varied in the formulations, the table shows this variation by specifying a percentage in relation to the amount of $TiO_2$ used in the reference formulation (test 1-1). For example, test 1-2 implements an amount of titanium dioxide reduced by 20% compared to the reference (test 1-1), i.e., 80% of the amount of $TiO_2$ in the reference formulation.

the polymers of tests 1-5 to 1-12 allow at least a partial compensation for the loss in $TiO_2$, their UV absorbancy spectrum being superior overall to that of test 1-2 (reference—20% $TiO_2$), the polymer of test 1-5 enables a complete compensation for the 20% loss in $TiO_2$ compared to the reference (test 1-1), its UV absorbancy spectrum being equivalent overall to that of test 1-1 (reference) and the polymers of tests 1-11 and 1-12 not only enable a compensation, but in addition, they improve the UV absorbancy of the formulation, their UV absorbancy spectrum being greater than that of test 1-1 (reference with 100% $TiO_2$).

Thus, it is demonstrated that despite the decrease in the amount of $TiO_2$ in the sun cream, the addition of one of the polymers according to the invention enables a compensation, at least in part, in the UV absorbancy of sun creams.

Organoleptic, Brookfield Viscosity & Consistency Properties:

TABLE 2

| | | | | | | Ingredient C-15 | | | | | |
|---|---|---|---|---|---|---|---|---|---|---|---|
| | Ingredient | Aqueous solution | | Monomeric composition (mass %) | | | | | | | |
| Test | C-14 Y $TiO_2$ | % Active ingredient | Z (%) | Acrylic acid | Methacrylic acid | Monomer I | Characteristics of Monomer I: | | | | Mw (g/mol) |
| | | | | | | | R | R' | m | N | |
| 1-1 (REF) | 5.0 100% | NA | — | — | — | — | NA | NA | NA | NA | NA |
| 1-2 (REF) | 4.0 80% | NA | — | — | — | — | NA | NA | NA | NA | NA |
| 1-3 (PA) | 4.0 80% | 25.0 | 2.0* | NA | NA | NA | NA | NA | NA | NA | NA |
| 1-4 (OINV) | 4.0 80% | 25.0 | 2.0 | 6.03 | — | 93.97 | Methacrylate | $CH_3$ | 0 | 113 | 52,000 |
| 1-5 (INV) | 4.0 80% | 25.0 | 2.0 | 8.14 | 2.79 | 89.07 | Methacrylate | H | 15 | 46 | 62,000 |
| 1-6 (INV) | 4.0 80% | 25.0 | 2.0 | — | 7.50 | 92.50 | Methacrylate | H | 15 | 46 | 120,000 |
| 1-7 (INV) | 4.0 80% | 25.0 | 2.0 | 8.14 | 2.79 | 89.07 | Methacrylate | H | 15 | 46 | 142,000 |
| 1-8 (INV) | 4.0 80% | 25.0 | 2.0 | 8.14 | 2.79 | 89.07 | Methacrylate | H | 15 | 46 | 259,000 |
| 1-9 (INV) | 4.0 80% | 25.0 | 2.0 | 8.14 | 2.79 | 89.07 | Methacrylate | H | 15 | 46 | 375,000 |
| 1-10 (INV) | 4.0 80% | 25.0 | 2.0 | 8.14 | 2.79 | 89.07 | Methacrylate | H | 15 | 46 | 770,000 |
| 1-11 (INV) | 4.0 80% | 25.0 | 1.0 | 8.14 | 2.79 | 89.07 | Methacrylate | H | 15 | 46 | 1,560,000 |
| 1-12 (INV) | 4.0 80% | 25.0 | 1.0 | 8.14 | 2.79 | 89.07 | Methacrylate | H | 15 | 46 | 11,025,000 |
| 1-13 (INV) | 5.0 100% | 25.0 | 2.0 | 8.14 | 2.79 | 89.07 | Methacrylate | H | 15 | 46 | 375,000 |
| 1-14 (CONT) | — | 25.0 | 2.0 | 8.14 | 2.79 | 89.07 | Methacrylate | H | 15 | 46 | 375,000 |
| 1-15 (CONT) | — | 25.0 | 2.0 | 8.14 | 2.79 | 89.07 | Methacrylate | H | 15 | 46 | 11,025,000 |

Figure 2:
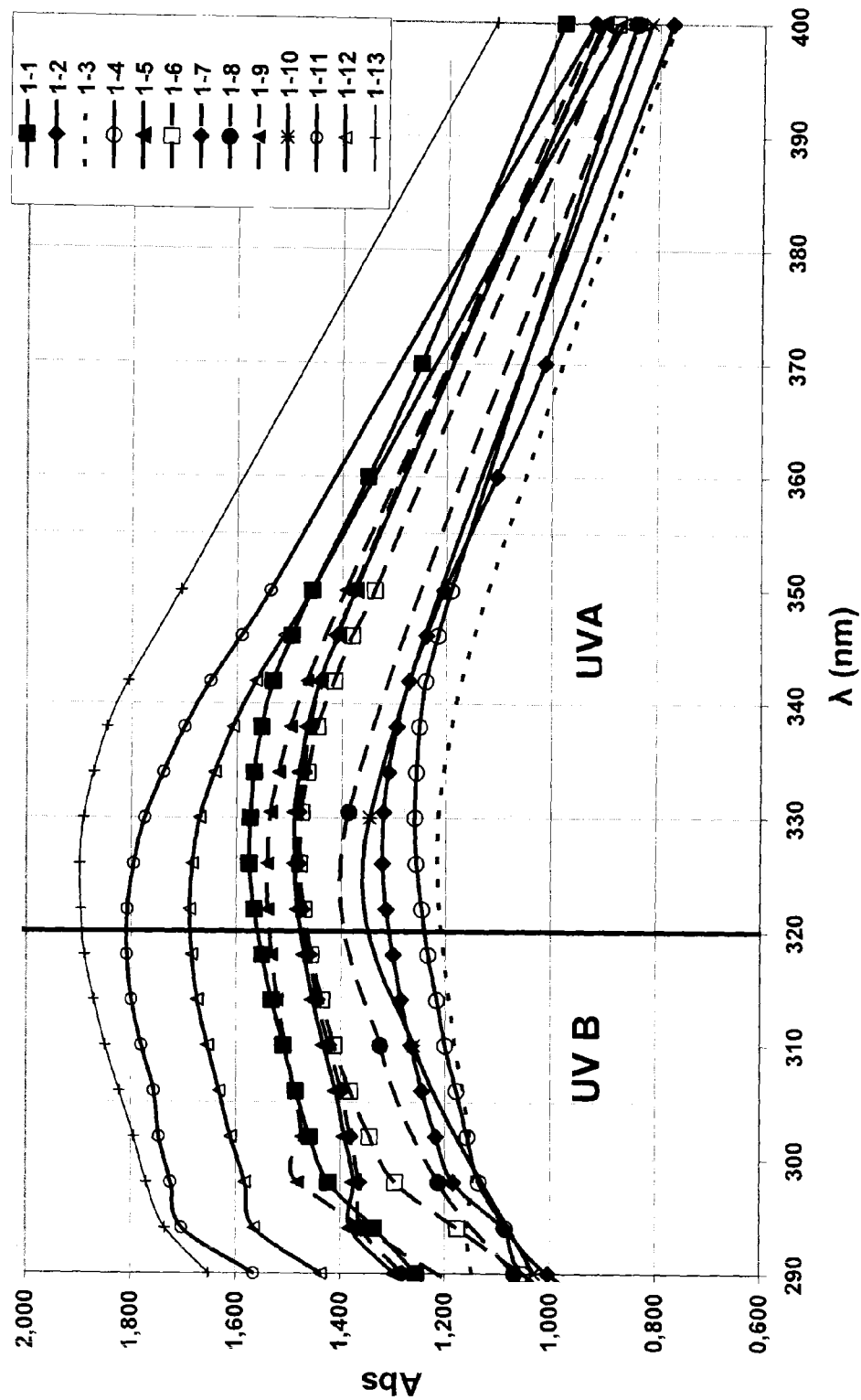
FIG. 2 shows the UV-A and UV-B absorbance spectra described in Example 1.

REF: Reference
PA: Prior Art
INV: Invention
OINV: Outside the invention
CONT: Control
NA: not applicable
*Test 1-3: Ingredient C-15 here is a dispersant for $TiO_2$ of the Polyglyceryl-10 Decaoleate type The UV-A and UV-B absorbance spectras are presented in FIGS. 1 and 2.

FIG. 1 shows that:

by decreasing the amount of titanium dioxide by 20% by weight in the formulation, the UV absorbancy of the formulation is reduced (test 1-2 vs test 1-1) and the polymers according to the invention are not UV filters (tests 1-13 and 1-14), that is, they are not substances that are capable to filter UV radiations.

FIG. 2 shows that:

the polymers of tests 1-3 and 1-4 do not compensate for the 20% reduction in $TiO_2$, their UV absorbancy spectrum being inferior overall to that of test 1-2 (reference—20% $TiO_2$),

TABLE 3

| Test No. | REF/PA/ INV | Organoleptic properties at t = month | Brookfield Viscosity (cPs, 20 rpm, 25° C.) - Measurement of the consistency G* (Pa, 1 Hz) at t = month |
|---|---|---|---|
| 1-1 | REF | Organoleptic: Slump: good coverage Texture: smooth Odour: odourless Colour: homogeneous Surface: smooth | VB = 28,950 G* = 600 |

TABLE 3-continued

| Test No. | REF/PA/INV | Organoleptic properties at t = month | Brookfield Viscosity (cPs, 20 rpm, 25° C.) - Measurement of the consistency G* (Pa, 1 Hz) at t = month |
|---|---|---|---|
| 1-3 | PA | Organoleptic: Slump: good coverage Texture: granular Odour: odourless Colour: homogeneous Surface: smooth | VB = 22,300 G* = 400 |
| 1-9 | INV | Organoleptic: Slump: good coverage Texture: smooth Odour: odourless Colour: homogeneous Surface: smooth | VB = 19,400 G* = 250 |

Evaluation of the Stability of the Formulations:

The stability test at t=1 week and at t=3 months carried out on a formulation containing the polymer of test 1-1 (reference) and in parallel on a formulation containing the polymer of test 1-9 shows no significant difference in all the criteria considered, i.e. no dephasing, creaming, liquid release and no bleeding or sedimentation.

For the two formulations, it is noted that the number of freeze-thaw cycles before destabilization is identical, i.e., five.

Example 2—Sprayable Solar Lotion

This example illustrates the implementation of a polymer according to the invention in a sprayable solar lotion, which is characterized by a particular rheological profile, based on the following ingredients (the figures in the last column indicate the mass percentages in relation to the total weight of the composition):

TABLE 4

| Phase A | A-1 Silkflo ® 366 NF (Lipo Chemicals Ltd)) | 5.0 |
|---|---|---|
| | A-2 Ultracas ® G-20 Guerbet Ester (Lubrizol) | 0.5 |
| Phase B | B-3 DI Water | QSP 100 |
| | B-4 Pemulen ® TR2 Polymer (Lubrizol) | 0.15 |
| | B-5 Carbopol ® ETD 2050 Polymer (Lubrizol) | 0.1 |
| | B-6 D-Panthenol ® (BASF) | 0.8 |
| | B-7 Propylene Glycol | 2.0 |
| | B-8 Polymer | Z |
| | B-9 Parsol ® TX (DSM) | Y |
| Phase C | C-10 DI Water | 20.0 |
| | C-11 Silsense ® copolyol-1 silicone(Lubrizol) | 5.0 |
| Phase D | D-12 NaOH (18%) | 0.3 |
| Phase E | E-13 Phenonip ® (Clariant) | 0.5 |

Formulation Preparation Protocol:

Phase A: all the ingredients of Phase A are mixed;

Phase B: B-3 is then introduced into another beaker, and then B-4 and B-5 are successively dispersed. Ingredients B-6, B-7 are then added, possibly B-8 and finally B-9.

Phase B is then introduced into phase A.

Phase C: C-11 is diluted in C-10. This mixture is introduced into the Phase A/Phase B mixture.

The formula is homogenized for 1 minute.

the formulation is neutralized with D-12 (pH=5.7 to 6.2). Finally, it is added to mixture E-13.

Table 5 summarizes all the polymers that were used as ingredient B-8 as part of the tests in the present example 2.

It is noted that the amount of titanium dioxide indicated in the table is expressed as magnitude Y, i.e. a mass percentage in relation to the total weight of the composition. For example, if Y is equal to 0.5%, 0.5 g of B-8 is added for a formulation of 100 g of finished product.

Also, to the extent that the amount of titanium dioxide is varied in the formulations, the table shows this variation by specifying a percentage in relation to the amount of $TiO_2$ used in the reference formulation (test 2-1).

For example, test 2-5 implements an amount of titanium dioxide reduced by 20% compared to the reference (test 2-1), i.e., 80% of the amount of TiO2 in the reference formulation.

TABLE 5

| | | Ingredient B-8 | | | | | | | | |
|---|---|---|---|---|---|---|---|---|---|---|
| | Ingredient B-9 $TiO_2$ | Aqueous solution % Active ingredient | Z (%) | Composition (mass %) | | | Characteristics of Monomer I | | | Mw (g/mol) |
| Test | | | | Acrylic acid | Methacrylic acid | Monomer I | R | R' | m | n | |
| 2-1 (REF) | Y % 0.5 100 | NA | 0 | — | — | — | NA | NA | NA | NA | NA |
| 2-2 (REF) | Y % 0.4 80 | NA | 0 | — | — | — | NA | NA | NA | NA | NA |
| 2-3 (REF) | Y % 0.3 60 | NA | 0 | — | — | — | NA | NA | NA | NA | NA |
| 2-4 (PA) | Y % 0.4 80 | 25.0 | 0.4* | 0.0 | 0.0 | 0.0 | NA | NA | NA | NA | NA |
| 2-5 (INV) | Y % 0.4 80 | 25.0 | 0.4 | 8.14 | 2.79 | 89.07 | Methacrylate | H | 15 | 46 | 375,000 |
| 2-6 (INV) | Y % 0.3 60 | 25.0 | 0.4 | 8.14 | 2.79 | 89.07 | Methacrylate | H | 15 | 46 | 375,000 |
| 2-7 (INV) | Y % 0.4 80 | 25.0 | 0.4 | 8.14 | 2.79 | 89.07 | Methacrylate | H | 15 | 46 | 1,100,000 |

TABLE 5-continued

| | | | | Ingredient B-8 | | | | | | | |
|---|---|---|---|---|---|---|---|---|---|---|---|
| | Ingredient | Aqueous solution | | Composition (mass %) | | | Characteristics of Monomer I | | | | Mw |
| Test | B-9 TiO$_2$ | % Active ingredient | Z (%) | Acrylic acid | Methacrylic acid | Monomer I | R | R' | m | n | (g/mol) |
| 2-8 (INV) | Y 0.4 % 80 | 25.0 | 0.4 | 5.06 | — | 94.94 | Methacrylate | H | — | 113 | 3,100,000 |

REF: Reference
PA: Prior Art
INV: Invention
OINV: Outside the invention
CONT: Control
NA: not applicable
*The additive of the prior art used is a dispersant of the Polyglyceryl-10 Decaoleate type The UV-A and UV-B absorbance spectras are presented in FIG. 3.

Figure 3:
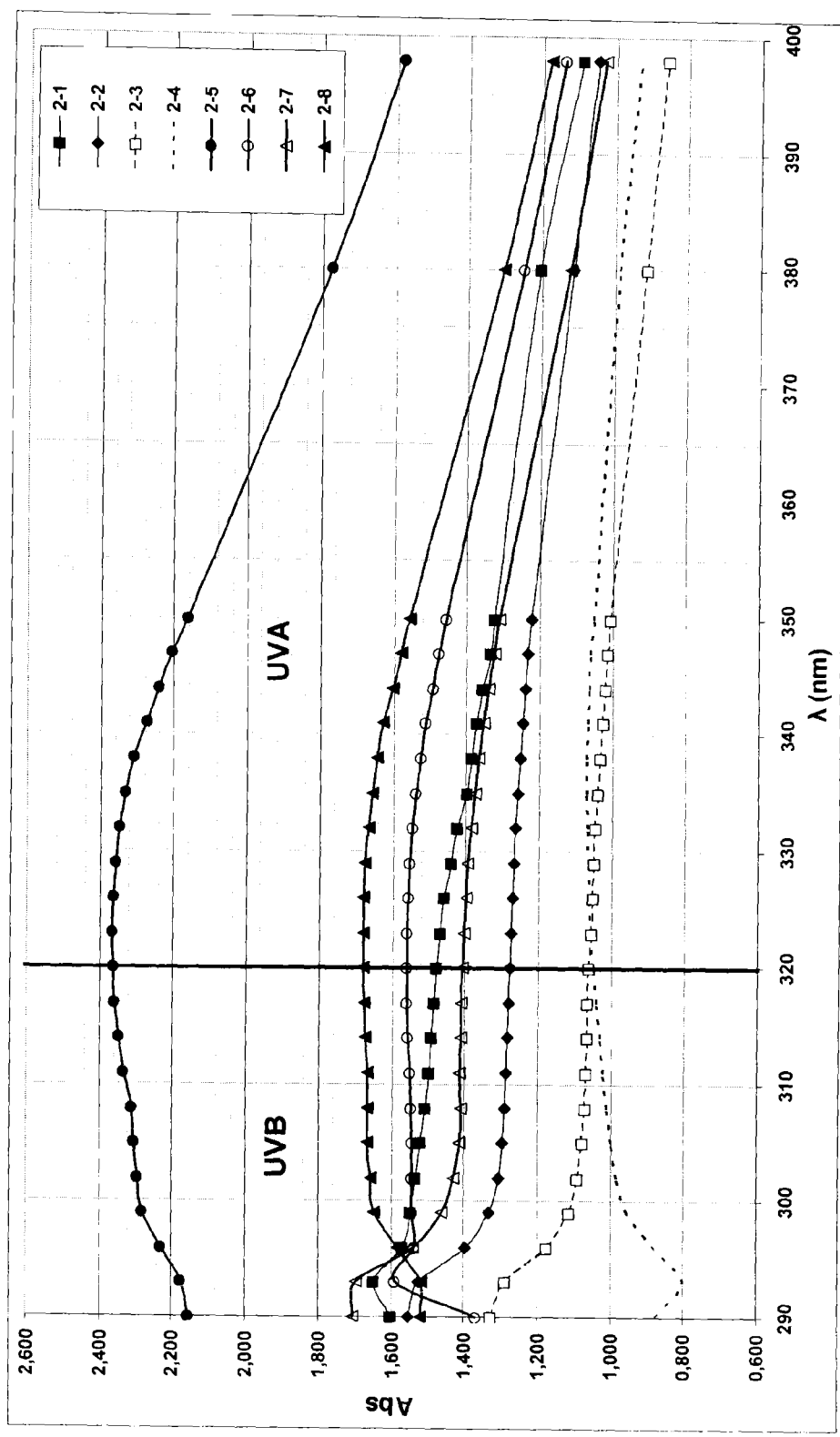
FIG. 3 shows the UV-A and UV-B absorbance spectra described in Example 2.

FIG. 3 shows that:
- by decreasing the amount of titanium dioxide by 20% or 40% by weight in the formulation, the absorbancy of the formulation is significantly reduced (test 2-2 and test 2-3 vs test 2-1);
- the polymer of test 2-4 (prior art) does not compensate for the 20% reduction in TiO$_2$, its UV absorbancy spectrum being inferior overall to that of test 2-2 (reference—20% TiO$_2$);
- the polymers of tests 2-5 to 2-8 allow at least a partial compensation for the loss of TiO$_2$, their UV absorbancy spectrum being superior overall to that of test 2-2 (reference—20% TiO$_2$) and
- the polymers of tests 2-5, 2-6 and 2-8 not only enable a compensation for the 20% loss of TiO$_2$, but in addition, they improve the absorbancy of the formulation over the UV spectrum, their UV absorbancy spectrum being greater than that of test 2-1 (reference with 100% TiO$_2$).

Organoleptic, Brookfield Viscosity & Consistency Properties:

TABLE 6

| Test No. | REF/ INV | Organoleptic properties at t = 1 month | Brookfield Viscosity (cPs, 20 rpm, 25° C.) Measurement of the consistency G* (Pa, 1 Hz) at t = 1 month |
|---|---|---|---|
| 2-1 | REF | Organoleptic: Slump: good coverage Texture: fluid Odour: odourless Colour: homogeneous Surface: smooth | VB: 1,420 G* = 19.5 |
| 2-6 | INV | Organoleptic: Slump: good coverage Texture: fluid Odour: odourless Colour: homogeneous Surface: smooth | VB = 840 G* = 13.6 |

Evaluation of the Stability of the Formulations:

The stability test at t=1 week carried out on a formulation containing the polymer of test 2-1 (reference) and in parallel on a formulation containing the polymer of test 2-6 (invention) shows no significant difference in all the criteria considered, i.e. no dephasing, creaming, liquid release and no bleeding or sedimentation.

The stability test at t=3 months carried out on a formulation containing the polymer of test 2-1 (reference) and in parallel on a formulation containing the polymer of test 2-6 (invention) shows a difference concerning the bleeding criterion: whereas the formulation containing the reference polymer shows a slight bleeding at t=3 months, this instability is not observed in the formulation containing a polymer according to the invention.

For the two formulations, it is noted that the number of freeze-thaw cycles before destabilization is identical, i.e., five.

It is thus shown that the additives according to the invention are performing not only in formulations of the cream type (example 1), but also in sprayable lotions (example 2).

Despite a decrease of 20% or even 40% by weight in the initial amount of UV filters of the TiO$_2$ type, the addition of additives according to the invention enables maintaining, at least in part, or even increasing significatively in the UV absorbancy performances of sunscreen compositions (creams or lotions for example).

Example 3—Sun Cream

This example illustrates the use of an agent according to the invention in an SFP 25 sun cream formulation based on the following ingredients (the figures in the last column indicate the masses in grams in relation to the total weight of the composition):

TABLE 7

| Phase A | A-1 DI Water | QSP 100 |
|---|---|---|
| | A-2 Protachem Na2-P (Protameen) | 0.05 |
| | A-3 Methocel ® E4M PREM (Dow) | 0.1 |
| | A-4 AMP-Ultra ™ PC 2000 (Dow) | 0.3 |
| | | (Qsp pH 6.70-7.00) |
| | A-5 Butylene glycol | 1.0 |
| | A-6 Glycerin | 2.0 |
| | A-7 Glucam E-20 Humectant (Lubrizol) | 2.0 |
| Phase B | B-8 Crodamol DA-LQ-(Croda) | 4.0 |
| | B-9 Shercemol ™ CO Ester (Lubrizol) | 2.0 |
| | B-10 Crodamol DIPD-LQ-(MV) (Croda) | 1.0 |
| | B-11 Glucate ™ SS Emulsifier (Lubrizol) | 0.1 |
| | B-12 Pemulen ® TR-1 (Lubrizol) | 0.2 |
| | B-13 Carbopol ® Ultrez 21 (Lubrizol) | 0.2 |

TABLE 7-continued

| | |
|---|---|
| Phase C C-14 Solaveil CT 200 (Croda) | Y |
| C-15 Polymer | Z |
| Phase D D-16 Nipaguard PDU (Induchem) | 1.0 |

Formulation Preparation Protocol:

Phase A: the different ingredients are introduced under agitation and the medium is heated to 65° C.;

Phase B: In another beaker, all the ingredients are mixed, except B-12 and B-13, and they are heated to 65° C. under agitation;

After obtaining a homogeneous phase B, ingredient B-12 as well as B-13 are dispersed under agitation;

Phases A and B are mixed so as to obtain a viscous emulsion;

Phase C: under very gentle agitation, ingredient C-15 is added if it is present, and then ingredient C-14, which is titanium dioxide sold by the company Croda, and is in the form of a dispersion in a cosmetic oil;

the formulation is completed by adding ingredient D-16 and the pH is measured and a check is made to ensure that it is in the 6.7-7.0 range.

Table 8 summarizes all the polymers used as ingredient C-15.

It is noted that the amount of titanium dioxide indicated in the table is expressed as magnitude Y, i.e. a mass percentage in relation to the total weight of the composition.

For example, if Y is equal to 15%, 15 g of C-14 are added for a formulation of 100 g of finished product.

Also, to the extent that the amount of titanium dioxide is varied in the formulations, the table indicates this variation by specifying a percentage in relation to the amount of $TiO_2$ used in the reference formulation (test 3-1).

For example, test 3-3 implements an amount of titanium dioxide reduced by 20% compared to the reference (test 3-1), i.e., 80% of the amount of TiO2 in the reference formulation.

Figure 4:
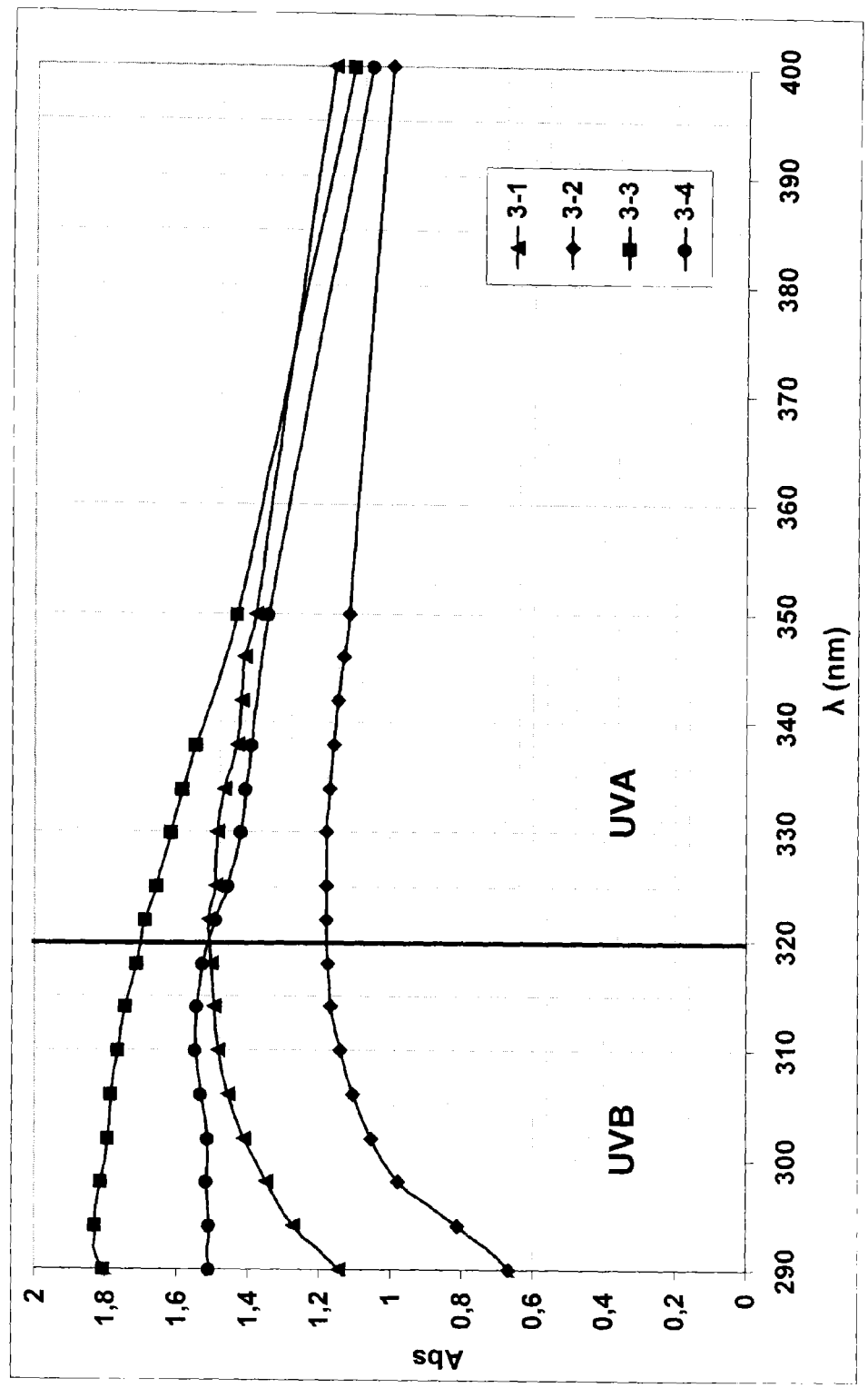
FIG. 4 shows the UV-A and UV-B absorbance spectra described in Example 3.

The UV-A and UV-B absorbance spectras are presented in FIG. 4.

FIG. 4 shows that the polymers of tests 3-3 and 3-4 not only enable a compensation for the 20% loss of $TiO_2$, but in addition, they improve the UV absorbancy of the formulation (its absorbancy spectrum being greater than that of test 3-2, reference).

Example 4—Zinc Oxide Sun Cream

This example illustrates the use of an agent according to the invention in a sun cream formulation based on the following ingredients (the figures in the last column indicate the masses in grams in relation to the total weight of the composition):

TABLE 9

| | | |
|---|---|---|
| Phase A | A-1 DI Water | QSP 100 |
| | A-2 Protachem Na2-P (Protameen) | 0.05 |
| | A-3 Methocel ® E4M PREM (Dow) | 0.1 |
| | A-4 AMP-Ultra ™ PC 2000 (Dow) | 0.3 |
| | | (Qsp pH 6.70-7.00) |
| | A-5 Butylene glycol | 1.0 |
| | A-6 Glycerin | 2.0 |
| | A-7 Glucam E-20 Humectant (Lubrizol) | 2.0 |
| Phase B | B-8 Crodamol DA-LQ-(Croda) | 4.0 |
| | B-9 Shercemol ™ CO Ester (Lubrizol) | 2.0 |
| | B-10 Crodamol DIPD-LQ-(MV) (Croda) | 1.0 |
| | B-11 Glucate ™ SS Emulsifier (Lubrizol) | 0.1 |
| | B-12 Pemulen TR-1 (Lubrizol) | 0.2 |
| | B-13 Carbopol Ultrez 21 (Lubrizol) | 0.2 |
| Phase C | C-14 Nanox ® 200 | Y |
| | C-15 Polymer | Z |
| Phase D | D-16 Nipaguard PDU (Induchem) | 1.0 |

The protocol for the preparation of the formulation is identical to that of example 1. Titanium dioxide is replaced by zinc oxide (commercially available) in the powder form.

Table 10 summarizes all the polymers used as ingredient C-15.

TABLE 8

| | | Ingredient C-15 | | | | | | | | |
|---|---|---|---|---|---|---|---|---|---|---|
| | | Aqueous solution | | Monomeric composition (mass %) | | | | | | |
| | C-14 | % Active | Z | Acrylic | Methacrylic | | Characteristics of Monomer I | | | Mw |
| Test | Y (%) | ingredient | (%) | acid | acid | Monomer I | R | R' | m | n | (g/mol) |
| 3-1 (REF) | 15.0 100% | NA | NA | — | — | — | NA | NA | NA | NA | NA |
| 3-2 (REF) | 12.0 80% | NA | NA | — | — | — | NA | NA | NA | NA | NA |
| 3-3 (INV) | 12.0 80% | 25.0 | 0.78 | 8.14 | 2.79 | 89.07 | Methacrylate | H | 15 | 46 | 375,000 |
| 3-4 (INV) | 12.0 80% | 25.0 | 0.78 | 8.14 | 2.79 | 89.07 | Methacrylate | H | 15 | 46 | 770,000 |

REF: Reference
PA: Prior Art
INV: Invention
OINV: Outside the invention
CONT: Control
NA: not applicable

TABLE 10

| | | Aqueous solution | | Monomeric composition (mass %) | | | Ingredient C-15 | | | | |
|---|---|---|---|---|---|---|---|---|---|---|---|
| | C-14 | % Active | Z | Acrylic | Methacrylic | | Characteristics of Monomer I | | | | Mw |
| Test | Y (%) | ingredient | (%) | acid | acid | Monomer I | R | R' | m | n | (g/mol) |
| 4-1 (REF) | 5.0 100% | NA | NA | — | — | — | NA | NA | NA | NA | NA |
| 4-2 (REF) | 4.0 80% | NA | NA | — | — | — | NA | NA | NA | NA | NA |
| 4-3 (INV) | 5.0 100% | 25.0 | 2.00 | 8.14 | 2.79 | 89.07 | Methacrylate | H | 15 | 46 | 375,000 |
| 4-4 (INV) | 4.0 80% | 25.0 | 2.00 | 8.14 | 2.79 | 89.07 | Methacrylate | H | 15 | 46 | 375,000 |

REF: Reference
PA: Prior Art
INV: Invention
OINV: Outside the invention
CONT: Control
NA: not applicable The UV-A and UV-B absorbance spectras are presented in FIG. 5.

Figure 5:
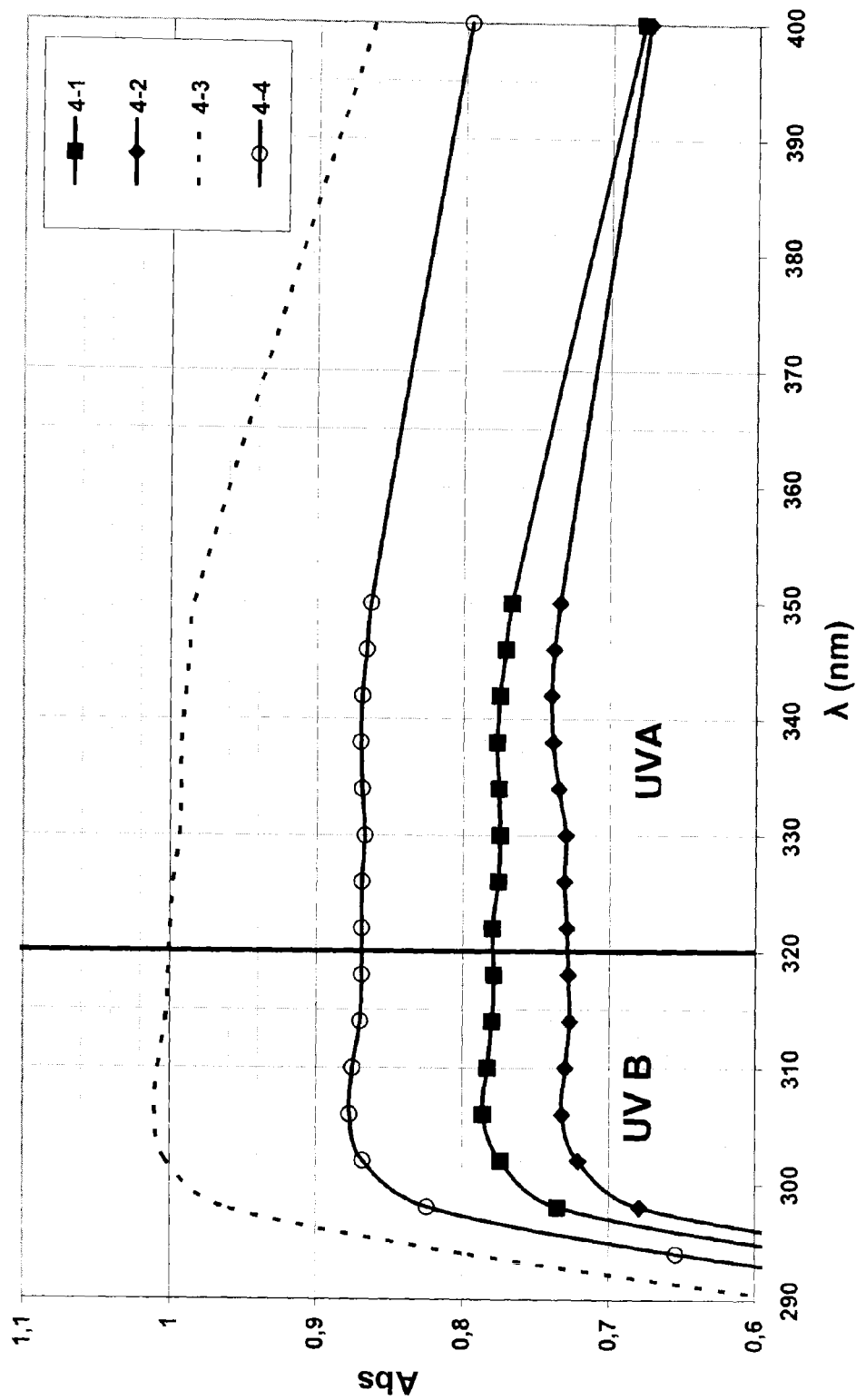
FIG. 5 shows the UV-A and UV-B absorbance spectra described in Example 4.

FIG. 5 shows that the polymer of tests 4-3 and 4-4 not only enables a compensation for the 20% loss of ZnO, but in addition, it improves the UV absorbancy of the formulation (its absorbancy spectrum being greater than that of test 4-2, reference).

It is thus shown that the additives according to the invention are effective in formulations of sun cream type (examples 1, 3 and 4) regardless of the form in which the titanium dioxide particles are present (powder or dispersed in an oil) or the zinc oxide particles are present (powder) as UV-absorbing filters, or again, in cosmetic compositions of sprayable type (example 2).

The invention claimed is:

1. A composition comprising from 0.1 to 50% by weight, in relation to the total weight of the composition, titanium dioxide and/or zinc oxide and at least one water soluble copolymer comprising:
   (a) 5.06 to 10.93% by weight of at least one acrylic acid monomer and/or one methacrylic acid monomer and/or their salt(s),
   (b) 89.07 to 93.97% by weight of at least one monomer of formula (I):

$$R-X-R' \qquad (I)$$

wherein:
   R represents methacrylate,
   R' designates hydrogen,
   X represents a structure with n unit(s) of ethylene oxide ("EO") and m unit(s) of propylene oxide ("PO"), arranged regularly or randomly,
   m and n are 2 integers comprised between 0 and 100, at least one of which is non-zero,
   wherein said water soluble copolymer has a molecular mass ranging from 62,000 and 11,025,000 g/mol as determined by GPC;
   wherein said composition has a higher UV absorbency value at wavelengths between 290 and 400 nm, compared to an otherwise identical sunscreen or cosmetic having a same amount of pigment particles that does not contain said water-soluble copolymer; and
   wherein said composition is in a physiological or cosmetically acceptable form.

2. The composition according to claim 1, wherein said water-soluble copolymer has a molecular mass ranging from 300,000 and 1,000,000 g/mol.

3. The composition according to claim 1, wherein said water-soluble copolymer has a molecular mass ranging from 62,000 and 500,000 g/mol.

4. The composition according to claim 1 wherein said water-soluble copolymer is such that n and m are two integers, at least one of which is non-zero and n+m>17.

5. The composition according to claim 1, wherein said composition comprises from 0.05 to 5% by weight of active matter of said copolymer in relation to the total weight of the composition.

6. The composition according to claim 1, wherein said composition comprises from 0.2 to 50% by weight of titanium dioxide and/or zinc oxide pigment particles.

7. The composition according to claim 1, which further comprises at least one additional organic photoprotective UV-A and/or UV-B agent, and/or at least one hydrophilic, lipophilic or non-water-soluble solvent.

8. The composition according to claim 1, further comprising at least one cosmetic additive selected from the group consisting of softeners, humectants, opacifiers, stabilizers, emollients, silicones, anti-foaming agents, perfumes, preservative agents, anionic, cationic, non-ionic, zwitterionic or amphoteric surfactants, fillers, propellant agents, acidifying or alkalinising agents or other cosmetically acceptable ingredient.

9. The composition according to claim 1 in the form of a white or coloured cream, an ointment, a milk, a lotion, a serum, a paste, a powder, a solid stick, an aerosol, a foam or a spray.

10. A sunscreen or cosmetic comprising the composition of claim 1 that has a higher UV absorbency value at wavelengths between 310 and 340 nm, compared to an otherwise identical sunscreen or cosmetic having a same amount of pigment particles, that does not contain said water-soluble copolymer.

11. A method for making a sunscreen comprising admixing the composition of claim 1 with at least one cosmetically acceptable ingredient or incorporating said composition into a cosmetically acceptable support.

12. A method for absorbing or filtering UV radiation comprising contacting skin or another surface with the composition of claim 1.

13. A sunscreen or cosmetic comprising the composition of claim 1 and a physiologically or cosmetically acceptable medium which is suitable for application to skin.

14. The sunscreen or cosmetic of claim 13 in the form of an O/W, W/O, W/O/W, O/W/O or O/O/W emulsion.

15. The sunscreen or cosmetic of claim 13 in the form of an aerosol, spray or foam.

16. The sunscreen or cosmetic of claim 13 in the form of a cream, ointment, milk, lotion, serum, paste, powder, or solid stick.

* * * * *